US012582590B2

(12) United States Patent
Yoshioka et al.

(10) Patent No.: US 12,582,590 B2
(45) Date of Patent: Mar. 24, 2026

(54) TRANSPARENT LIQUID COMPOSITION AND COSMETIC CONTAINING SAID COMPOSITION

(71) Applicant: SEIWA KASEI COMPANY, LIMITED, Higashiosaka (JP)

(72) Inventors: Masato Yoshioka, Higashiosaka (JP); Tatsuya Tsuboi, Higashiosaka (JP)

(73) Assignee: SEIWA KASEI COMPANY, LIMITED, Osaka (JP)

( * ) Notice: Subject to any disclaimer, the term of this patent is extended or adjusted under 35 U.S.C. 154(b) by 673 days.

(21) Appl. No.: 17/950,198

(22) Filed: Sep. 22, 2022

(65) Prior Publication Data

US 2023/0025852 A1 Jan. 26, 2023

Related U.S. Application Data

(63) Continuation of application No. PCT/JP2021/011920, filed on Mar. 23, 2021.

(30) Foreign Application Priority Data

Mar. 27, 2020 (JP) ................................ 2020-058669

(51) Int. Cl.

| | |
|---|---|
| ***A61K 8/49*** | (2006.01) |
| ***A61K 8/34*** | (2006.01) |
| ***A61K 8/365*** | (2006.01) |
| ***A61K 8/42*** | (2006.01) |
| ***A61K 8/64*** | (2006.01) |
| ***A61Q 5/00*** | (2006.01) |
| ***A61Q 5/12*** | (2006.01) |

(52) U.S. Cl.

CPC ............ *A61K 8/4913* (2013.01); *A61K 8/345* (2013.01); *A61K 8/365* (2013.01); *A61K 8/42* (2013.01); *A61K 8/645* (2013.01); *A61Q 5/002* (2013.01); *A61Q 5/12* (2013.01); *A61K 2800/262* (2013.01)

(58) Field of Classification Search

CPC ...... A61K 8/4913; A61K 8/345; A61K 8/365; A61K 8/42; A61K 8/645; A61K 2800/262; A61K 8/44; A61K 8/64; A61K 8/65; A61Q 5/002; A61Q 5/12

See application file for complete search history.

(56) References Cited

U.S. PATENT DOCUMENTS

| | | | | |
|---|---|---|---|---|
| 3,958,581 | A | 5/1976 | Abegg et al. | |
| 5,328,685 | A * | 7/1994 | Janchitraponvej ..... | A61K 8/898 424/70.11 |
| 5,556,615 | A | 9/1996 | Janchitraponvej et al. | |
| 2006/0127350 | A1* | 6/2006 | Heegaard ............. | C08G 83/003 424/78.17 |
| 2008/0113892 | A1* | 5/2008 | Barnhart ................ | C11D 1/528 510/138 |
| 2012/0288463 | A1 | 11/2012 | Yoshioka et al. | |
| 2017/0246097 | A1* | 8/2017 | Calvert .................... | A61K 8/19 |
| 2018/0271759 | A1 | 9/2018 | Brice et al. | |
| 2023/0025852 | A1* | 1/2023 | Yoshioka ................. | A61K 8/44 |

FOREIGN PATENT DOCUMENTS

| | | | | | |
|---|---|---|---|---|---|
| EP | 0 617 953 | A1 | | 10/1994 | |
| EP | 2 682 096 | A1 | | 1/2014 | |
| JP | 7-2629 | A | | 1/1995 | |
| JP | H08154625 | A | * | 6/1996 | ............ A23L 27/60 |
| JP | 2007-204375 | A | | 8/2007 | |
| JP | 2007-302615 | A | | 11/2007 | |
| JP | 2012-56926 | A | | 3/2012 | |
| JP | 4927986 | B2 | | 5/2012 | |
| JP | 2012-111709 | A | | 6/2012 | |
| JP | 4947749 | B1 | | 6/2012 | |
| JP | 5288426 | B1 | | 9/2013 | |
| JP | 2018-520088 | A | | 7/2018 | |
| JP | 2019081747 | A | * | 5/2019 | .............. A61K 8/36 |
| WO | WO 2012/140725 | A1 | | 10/2012 | |
| WO | WO 2013/073350 | A1 | | 5/2013 | |

OTHER PUBLICATIONS

Ogorzalek "Surfactant effects on protein structure examined by electrospray ionization mass spectrometry" Protein Science (1994), 3:1975 (Year: 1994).*

Cosmetic Ingredient Review "Safety Assessment of Keratin and Keratin-Derived Ingredients as Used in Cosmetics" (2015). (Year: 2015).*

Gekko "Mechanism of Polyol-induced Protein Stabilization: Solubility of Amino Acids and Diglycine in Aqueous Polyol Solutions" J. Biochem., 1981, 90, 1633-1641. (Year: 1981).*

Chinese Office Action for Chinese Application No. 202180023174.8, dated Dec. 29, 2023, with partial English translation.

Chinese Office Action for Chinese Application No. 202180023174.8, dated Apr. 25, 2024, with English translation.

(Continued)

*Primary Examiner* — Ali Soroush

*Assistant Examiner* — Rajan Pragani

(74) *Attorney, Agent, or Firm* — Birch, Stewart, Kolasch & Birch, LLP

(57) ABSTRACT

A transparent liquid composition is provided which has excellent handling properties when used in cosmetic production without causing increases in viscosity or precipitation of insoluble matter during storage, and which imparts hydrophobicity to damaged hair when added to a cosmetic, and is smooth, moist and soft so feels good during use; a cosmetic containing this transparent liquid composition is also provided. This transparent liquid composition is characterized by containing (A) a compound selected from a group consisting of peptides, amino acids and derivatives thereof, (B) fatty acid amidoamines, (C) gluconic acid and/or gluconolactones and (D) a polyhydric alcohol, wherein the mass ratio (C)/(B) of component (C) to component (B) is 0.5-2.0.

8 Claims, No Drawings

(56) References Cited

OTHER PUBLICATIONS

International Search Report (PCT/ISA/210), issued in PCT/JP2021/011920, dated Jun. 8, 2021.
Written Opinion of the International Searching Authority (PCT/ISA/237), issued in PCT/JP2021/011920, dated Jun. 8, 2021.
Extended European Search Report for European Application No. 21775902.6, dated Mar. 26, 2024.
Mintel, "Magic Help Conditioner," Nov. 28, 2018, 4 pages total.
English translation of the Chinese Office Action with Search Report dated Jun. 27, 2023 for Application No. 202180023174.8.
Japanese Office Action dated Jun. 8, 2023 for Application No. 2022-510526 with a partial English translation.

* cited by examiner

TRANSPARENT LIQUID COMPOSITION AND COSMETIC CONTAINING SAID COMPOSITION

CROSS REFERENCE TO RELATED APPLICATIONS

This application is a Continuation of PCT International Application No. PCT/JP2021/011920, filed on Mar. 23, 2021, which claims priority under 35 U.S.C. 119 (a) to Patent Application No. 2020-058669, filed in Japan on Mar. 27, 2020, all of which are hereby expressly incorporated by reference into the present application.

TECHNICAL FIELD

The present invention relates to a transparent liquid composition which contains a compound selected from the group consisting of a peptide, which is a protein hydrolysate, an amino acid, and a derivative of the peptide or the amino acid, a fatty acid amidoamine, gluconic acid and/or gluconolactone, and a polyhydric alcohol;

is a transparent composition for producing cosmetics not precipitating insoluble matter during storage; and gives excellent sensory properties to the hair; and relates to a cosmetic compounding the composition.

BACKGROUND ART

It is conceivable that hydrophobic substances such as 18-methyleicosanoic acid exist on the surface of healthy hair, and this hydrophobicity is greatly involved in sensory properties such as softness (flexibility), moist feeling, luster and smoothness of hair. However, when the hydrophobicity of the hair surface is lost due to chemical treatments such as perming and hair coloring or physical treatments such as brushing, the sensory properties are significantly reduced. Therefore, in order to suppress the deterioration of the above-mentioned sensory properties, various compositions for producing cosmetics having hair conditioning effects have been developed and blended into cosmetics.

Peptides, which are protein hydrolysates, and their derivatives have strong adsorptive power to hair, and are widely used for compositions for producing cosmetics having hair conditioning effects (Patent Document 1); and are formulated in hair treatment agents such as hair treatments and shampoos.

Furthermore, an ionic complex of a peptide or its derivative having an acidic amino acid as a constituent amino acid and fatty acid amidoamine, which is a cationic surfactant, has a high adsorptive power to hair and has excellent effects of making the surface of the hair, which has become less hydrophobic due to damage, hydrophobic, and imparting softness, moist feeling, smoothness, luster, etc. to hair. Hence, a cosmetic base material (composition for manufacturing cosmetics) containing said ion complex and cosmetics containing said cosmetic base material have been developed (Patent Documents 2 and 3).

However, when a cosmetic containing a composition containing the ion complex is applied to the hair, although it is excellent in the effect of imparting smoothness and luster due to the improvement of hydrophobicity, it is still insufficient in terms of imparting softness and moistness, and improvements in these effects have been desired.

Furthermore, the ion complex has low solubility in solvents that are allowed in the composition for cosmetic production, such as water and alcohols, and there have been cases that insoluble matter precipitates during storage, viscosity increases and it becomes semi-solid, and so on. Therefore, during the production of cosmetics, for example, in order to facilitate removal from the package, it is necessary to heat the composition to dissolve insoluble matter, reduce the viscosity, and the like, and there was a problem in terms of handling performance.

PRIOR ART DOCUMENT

Patent Document

Patent Document 1: JP-2007-302615A
Patent Document 2: Japanese Patent No. 4947749
Patent Document 3: Japanese Patent No. 5288426

SUMMARY OF THE INVENTION

Problem to be Solved by the Invention

An object of the present invention is to provide a transparent liquid composition suitable for use as a composition for manufacturing cosmetics, in which the problems of the prior art have been solved, and cosmetics. Specifically, the object is to provide a transparent liquid composition containing an ionic complex of a peptide, amino acid or a derivative thereof and a cationic surfactant, which imparts hydrophobicity to damaged hair and capable of imparting a favorable feeling of use such as softness, moistness, and smoothness, when compounded in a hair cosmetic, and in which the precipitation of insoluble matter during storage and the increase in viscosity are suppressed, and the handling property when manufacturing cosmetics is improved.

Means for Solving the Problem

As a result of intensive studies to solve the above problems, the present inventors have found that a composition containing an ion complex consisting of a peptide or a derivative thereof and a fatty acid amidoamine, which further contains gluconic acid and/or gluconolactone and a polyhydric alcohol in a specific mass ratio becomes a uniform liquid with low viscosity, and is stable without precipitation of insoluble (solids) even during storage; and that a cosmetic containing said composition is excellent in the effect of imparting softness and moist feeling as well as smoothness and luster, when applied to damaged hair.

The present inventors have also found that, even when amino acids or derivatives thereof are used instead of peptides or derivatives thereof as components constituting the ion complex, by compounding gluconic acid and/or gluconolactone and a polyhydric alcohol in a specific mass ratio, a transparent composition that becomes a uniform liquid with low viscosity and does not precipitate solids even during storage can be obtained, and cosmetics containing this composition are excellent in the effect of imparting smoothness and luster as well as softness and moistness, when applied to damaged hair. Thus, the present inventors have completed the present invention based on the finding.

That is, the present invention is a transparent liquid composition which contains (A) one or more compounds selected from the group consisting of peptides, peptide derivatives, amino acids and amino acid derivatives, (B) a fatty acid amidoamine represented by the following general formula (I), (C) gluconic acid and/or gluconolactone, and (D) a polyhydric alcohol, wherein (C)/(B), the mass ratio of (C) gluconic acid and/or gluconolactone to (B) fatty acid amidoamine, is 0.5 to 2.0 (claim 1).

[Chemical 1]

(I)

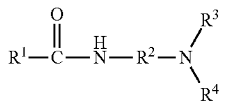

[In the formula, $R^1$ represents a saturated or unsaturated chain hydrocarbon having 11 to 25 carbon atoms or a saturated or unsaturated cyclic hydrocarbon having 11 to 25 carbon atoms, and $R^2$ represents an alkylene group having 1 to 3 carbon atoms, and $R^3$ and $R^4$ each represent an alkyl group having 1 to 3 carbon atoms.]

The contents of (A), (B), (C) and (D) are preferably 3 to 15% by mass, 5 to 15% by mass, 5 to 25% by mass, and 5 to 35% by mass respectively, based on the total mass of the composition (claim 2).

As the (A) one or more compounds selected from the group consisting of peptides, peptide derivatives, amino acids, and amino acid derivatives, compounds selected from the group consisting of vegetable protein hydrolysates, keratin hydrolysates, and derivatives thereof are preferred, from the viewpoint of high effect in imparting a favorable feeling of use such as softness and moistness, in addition to smoothness and luster of hair that has lost its hydrophobicity due to damage and has lost its smoothness and luster (claim 3).

As the (D) polyhydric alcohol, one selected from the group consisting of 1,3-butylene glycol, pentylene glycol, hexylene glycol and glycerin is preferable from the viewpoint of highly effect in suppressing precipitation of insoluble matter during storage (claim 4).

The present invention provides, in addition to the transparent liquid composition, a cosmetic containing the transparent liquid composition (claim 5).

Since this cosmetic has the property of improving the condition of the hair, the effect of the present invention is remarkably exhibited when it is compounded in a hair cosmetic for improving the condition of the hair, such as a hair treatment or a hair mist. Therefore, the present invention further provides a hair cosmetic that improves the condition of hair (claim 6).

Effect of the Invention

The transparent liquid composition of the present invention is a uniform, low-viscosity liquid containing an ion complex of one or more compounds selected from the group consisting of peptides, peptide derivatives, amino acids and amino acid derivatives and fatty acid amidoamines represented by general formula (I).

It imparts hydrophobicity to damaged hair, and can impart a favorable feeling of use such as smoothness, moistness, and softness, when applied to the hair.

It is a transparent liquid without precipitation of insoluble matter or an increase in viscosity during storage and is excellent in handling when producing cosmetics. Therefore, this composition can be preferably used for producing cosmetics such as hair cosmetics as a composition for producing cosmetics.

In addition, the cosmetic composition of the present invention containing the above composition is excellent in imparting hydrophobicity to damaged hair and imparting favorable feeling of use such as smoothness, moistness and softness when applied to hair, and therefore, it is suitably used as a cosmetic, especially a hair cosmetic such as a hair treatment or a hair mist that improves the condition of the hair.

MODES FOR CARRYING OUT THE INVENTION

Next, each component (A), (B), (C), (D) and other components constituting the transparent liquid composition of the present invention will be explained, and further, cosmetics containing the above composition will be explained.

[About Component (A)]

As described above, component (A) is a compound selected from the group consisting of peptides, peptide derivatives, amino acids and amino acid derivatives. One type of compound included in the above group may be used, or two or more types of compounds included in the above group may be used together.

(Peptide)

Peptides are protein hydrolysates. Peptides (protein hydrolysates) used as component (A), as disclosed in JP-61-183298A and JP-3-294298A, for example, can be produced by partially hydrolyzing proteins with acids, alkalis, enzymes, or a combination thereof.

As this peptide, those having a number average molecular weight in the range of 300 to 4,500 as measured by GPC (gel permeation chromatography) are preferred from the viewpoint of good adsorption to hair when the cosmetic containing the cosmetic composition of the present invention is applied to hair and high solubility in water and polyhydric alcohol. The number average molecular weight of the peptide can be controlled by adjusting the hydrolysis reaction conditions in the partial hydrolysis, i.e., pH, reaction temperature, reaction time, amount of enzyme used, and the like.

Examples of protein source (protein to be partially hydrolyzed) for producing the peptides include animal proteins, vegetable proteins, and proteins derived from microorganisms.

Examples of animal proteins include collagen (including its denatured gelatin), keratin, fibroin, sericin, casein, conchiolin, elastin, protamine, egg yolk protein and egg white protein of chickens and the like.

Examples of vegetable proteins include proteins contained in soybeans, wheat, rice (rice bran), sesame, peas, corn, potatoes and the like.

Examples of proteins derived from microorganisms include yeasts of the genus *Saccharomyces, Candida*, and Endomycopsis, yeast proteins isolated from yeast called beer yeast and sake yeast, and proteins isolated from mushrooms (basidiomycetes) and *chlorella, spirulina* protein derived from seaweed, and the like.

Among the peptides exemplified above, a vegetable protein hydrolyzate or a keratin hydrolyzate is preferably used as the component (A), because they are excellent in the effect of improving softness, moist feeling, luster and smoothness, when a cosmetic containing the composition of the present invention is applied to the hair. Among plant protein hydrolysates, hydrolysates of soybean, rice (rice bran), sesame, and pea proteins are particularly preferable from the viewpoint of being excellent in the above effects and being easily available.

(Derivatives of Peptides)

The peptide derivative as component (A) refers to a compound in which the amino group of the peptide is chemically modified (compound in which the hydrogen atom of the amino group is substituted with another functional group). That is, in derivatives of peptides, at least some of the hydrogen atoms of the terminal amino group of the peptide main chain and of the amino group in the amino acid side chain (hereinafter referred to as “side chain amino group”) are substituted with functional groups. Specific examples thereof include acylated peptides, quaternary ammonium peptides, silylated peptides, glyceryl peptides, and the like.

The acylated peptide refers to a compound in which a linear or branched saturated or unsaturated fatty acid or resin acid having 8 to 32 carbon atoms amide-bonded to at least part of the terminal amino group and side chain amino groups of the main chain of the peptide.

Examples of the linear or branched saturated or unsaturated fatty acid having 8 to 32 carbon atoms include lauric acid, myristic acid, coconut oil fatty acid, isostearic acid, stearic acid, undecylenic acid, and lanolin fatty acid. Resin acid is the main component of what is called rosin, and means a mixture of various isomers such as abietic acid, neoabietic acid, parastric acid, pimaric acid, isopimaric acid and dehydroabietic acid. The resin acids also include resin acid derivatives such as hydrogenated resin acids.

The peptides and peptide derivatives as component (A) also include salts thereof. Salts of acylated peptides include, for example, potassium salt, sodium salt, triethanolamine salt, 2-amino-2-methyl-1,3-propanediol salt, 2-amino-2-methyl-1-propanol salt, and the like. Such acylated peptides can be produced, for example, by the method disclosed in JP-59-101449A.

The quaternary ammonium peptide means a peptide in which a group represented by the following general formula (II) is bonded to at least part of the terminal amino group and side chain amino groups of the main chain of the peptide.

[Chemical 2]

(II)

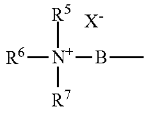

[In formula (II), $R^5$, $R^6$ and $R^7$ may be the same or different and represent an alkyl group having 1 to 22 carbon atoms or an alkenyl group having 2 to 22 carbon atoms, though one or two of $R^6$ and $R^7$ may be a hydroxyalkyl group having 1 to 3 carbon atoms or a benzyl group. B is a bond and represents a saturated hydrocarbon having 2 to 3 carbon atoms or a saturated hydrocarbon having 2 to 3 carbon atoms and having a hydroxyl group; and X represents a halogen atom.]

Such a quaternary ammonium peptide can be obtained by reacting the peptide with a quaternary ammonium compound under alkaline conditions. For example, it can be produced by the methods disclosed in JP-1982-130961A and Japanese Patent No. 2878287.

Examples of quaternary ammonium compounds that can be used in the production include

- glycidyl ammonium salts such as glycidyl stearyl dimethyl ammonium chloride, glycidyl coconut oil alkyl dimethyl ammonium chloride, glycidyl lauryl dimethyl ammonium chloride, and glycidyl trimethyl ammonium chloride;
- 3-halo-2-hydroxypropylammonium salts such as 3-chloro-2-hydroxypropyl stearyl dimethylammonium chloride, 3-chloro-2-hydroxypropyl coconut oil alkyldimethylammonium chloride, 3-chloro-2-hydroxypropyllauryl dimethylammonium chloride, 3-chloro-2-hydroxypropylethyldimethyl ammonium chloride, and 3-chloro-2-hydroxypropyltrimethylammonium chloride;
- 2-halo-ethylammonium salts such as 2-chloroethyltrimethylammonium chloride; and
- 3-halo-propylammonium salts such as 3-chloropropyltrimethylammonium chloride.

The silylated peptide is one in which a group represented by the following general formula (III) is bonded to at least part of the terminal amino group and side chain amino groups of the main chain of the peptide.

[Chemical 3]

(III)

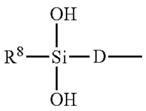

[In formula (III), $R^8$ represents an alkyl group having 1 to 3 carbon atoms, D is a bond and is methylene, propylene, or a group represented by $—CH_2OCH_2CH(OH)CH_2$ or $—(CH_2)_3OCH_2CH(OH)CH_2—$.]

The above silylated peptides can be produced, for example, by the methods disclosed in JP-1996-059424A and JP-1996-067608. Silylated peptides that can be used as component (A) include silicone-resinized peptides which are polymers of peptide in which a group represented by general formula (III) is bonded to an amino group, in addition to peptides in which a group represented by general formula (III) is bonded to an amino group. Silylated peptides containing the silicone-resinized peptides can also be used as component (A).

The glyceryl peptide is one in which a group represented by the following general formula (IV) or (V) is bonded to at least part of the terminal amino group and side chain amino groups of the main chain of the peptide.

[Chemical 4]

(IV)

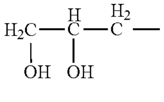

[Chemical 5]

(V)

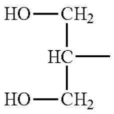

The glyceryl peptide can be produced, for example, by the method disclosed in JP-2005-306799A.

(Amino Acid)

The amino acid that can be used as the component (A) is a compound in which a basic group such as an amino group and an acidic group such as carboxyl group or sulfo group are bonded to both ends of a main chain consisting of one carbon atom or a main chain consisting of two or more carbon atoms, respectively. A basic amino acid having a basic group such as an amino group and an acidic amino acid having an acidic group, in a side chain branched from the main chain in addition to the amino group and acidic group bonded to the main chain, can also be used as component (A).

An amino acid forms an ionic complex with a fatty acid amidoamine (cationic surfactant) via an acidic group bonded to the main chain or side chain, thereby obtaining the effect of imparting adsorptivity and hydrophobicity to hair.

Both natural amino acids and non-natural amino acids can be used as amino acids.

Examples of natural amino acids include aspartic acid, glutamic acid, valine, glycine, alanine, leucine, isoleucine, serine, threonine, phenylalanine, asparagine, glutamine, tyrosine, methionine, cysteine, lysine, arginine, histidine, tryptophan, and proline.

Examples of non-natural amino acids include β-alanine, hydroxyproline, hydroxylysine, ornithine, citrulline, cystine, norleucine, α-aminobutyric acid, α-aminocaproic acid, taurine, and cystic acid.

(Derivatives of Amino Acids)

An amino acid derivative refers to a compound in which the amino group of an amino acid is chemically modified (a compound in which a hydrogen atom of the amino group is substituted with another functional group). Specifically, examples of amino acid derivatives include an acylated amino acid in which a saturated fatty acid having 1 to 22 carbon atoms, an unsaturated fatty acid having 3 to 22 carbon atoms, a cyclic fatty acid, or an aromatic carboxylic acid is bonded to an amino group;

- a sulfonylated amino acid in which an alkylsulfonic acid having 1 to 12 carbon atoms or an aromatic sulfonic acid is bonded to an amino group;
- an alkylated amino acid in which 1 or 2 hydrogen atoms of amino group are substituted with saturated or unsaturated alkyl group or aralkyl group having 1 to 22 carbon atoms;
- a betaine such as trimethylglycine;
- a silylated amino acid in which a group represented by general formula (III) is bonded to an amino group;
- a quaternary ammonium amino acid in which a group represented by general formula (II) is bonded to an amino group; and
- a glycerylated amino acid in which a group represented by general formula (IV) or (V) is bonded to an amino group Acylated amino acids, silylated amino acids, and quaternary ammonium amino acids can be produced by using an amino acid instead of peptide according to the methods of the above-mentioned patent documents, which disclose methods for producing the acylated peptides, silylated peptides, and quaternary ammonium peptides, respectively. An alkylated amino acid can be produced by an alkylation reaction of reacting an amino acid with a corresponding alkyl halide or a reductive amination reaction using a corresponding aldehyde and a reducing agent. Sulfonylated amino acids and glyceryl amino acids can be produced by the methods disclosed in Japanese Patent No. 6541118 and Japanese Patent No. 4391473, respectively.

Among the above compounds exemplified for use as component (A), vegetable protein hydrolysates, keratin hydrolysates and derivatives thereof are preferred, as peptides or derivatives thereof, from the viewpoint of their excellent effects in imparting sensory properties such as softness, moistness and smoothness to hair. As amino acids and derivatives thereof, sulfonylated amino acids and glyceryl amino acids are preferably used.

The preferred range of the content of component (A) in the transparent liquid composition of the present invention is not particularly limited, but is preferably 3 to 15% by mass, more preferably 10 to 15% by mass, based on the total amount of the composition.

[About Component (B) (Fatty Acid Amidoamine)]

The fatty acid amidoamine as component (B) is a cationic surfactant represented by the general formula (I), and is obtained by amide bonding the amino group of a dialkylaminoalkyleneamine to the carboxyl group of a fatty acid.

The fatty acid amidoamine in which $R^1$ in general formula (I) has a cyclic hydrocarbon can be produced, for example, by using rosin (pine resin) as a fatty acid to be reacted with a dialkylaminoalkyleneamine. Rosin is a non-volatile component of pine resin, which is contained in large amounts in plants of the pine family, and is mainly composed of various isomers called resin acids, which includes abietic acid, neoabietic acid, parastric acid, pimaric acid, isopimaric acid, and dehydroabietic acid. Further, if the stability as a composition and the safety when compounded in cosmetics are emphasized, it is preferable to use hydrogenated rosin obtained by hydrogenating rosin as the fatty acid.

The fatty acid amidoamine used in the present invention is not particularly limited as long as it is represented by the above general formula (I). Specific examples thereof include diethylaminoethylamide stearate (that is, stearamidoethyldiethylamine), diethylaminoethylamide palmitate, diethylaminoethylamide behenate, diethylaminoethylamide myristate, diethylaminoethylamide laurate, diethylaminoethylamide isostearate, dimethylaminopropylamide stearate (i.e. stearamidopropyldimethylamine), dimethylaminopropylamide palmitate, dimethylaminopropylamide behenate, dimethylaminopropylamide myristate, dimethylaminopropylamide laurate, dimethylaminopropylamide isostearate, diethylaminoethylamide resin acid (i.e. diethylaminoethylamine amide-bonded to carboxy group of resin acid), hydrogenated resin acid diethylaminoethylamide, resin acid dimethylaminopropylamide, and hydrogenated resin acid dimethylaminopropylamide.

Among the fatty acid amide amines exemplified above, as fatty acid amide amines that are industrially readily available and capable of sufficiently exhibiting the effects of the present invention, for example, diethylaminoethylamide stearate, dimethylaminopropyl amide stearate, diethylaminoethylamide palmitate, dimethylaminopropylamide palmitate, diethylaminoethylamide behenate, diethylaminoethylamide isostearate, and hydrogenated resin acid diethylaminoethylamide are preferred.

From the viewpoint of stability and versatility as a composition, diethylaminoethylamide stearate, diethylaminoethyl palmitate, dimethylaminopropylamide stearate, dimethylaminopropylamide palmitate, cetostearic acid diethylaminoethylamide obtained by mixing diethylaminoethylamide stearate and diethylaminoethylamide palmitate in a molar ratio of about 1:1 [i.e., cetearamidethyldiethylamine], and cetostearic acid dimethylaminopropylamide obtained by mixing dimethylaminopropylamide stearate and dimethylaminopropylamide palmitate in a molar ratio of about 1:1 [i.e., cetearamidpropyldimethylamine] are preferred. Among them, dimethylaminopropylamide stearate and diethylaminoethylamide stearate are particularly preferred.

The preferred range of the content of the component (B) fatty acid amidoamine in the transparent liquid composition of the present invention is not particularly limited, but the content is preferably 5 to 15% by mass, more preferably 7 to 12% by mass, based on the total amount of the composition.

[About Component (C) (Gluconic Acid and/or Gluconolactone)]

By compounding gluconic acid and/or gluconolactone as a component (C) with the component (A) and the component (B) in a specific mass ratio range with respect to the fatty acid amidoamine of the component (B), a uniform and transparent composition can be provided without precipitation of insoluble matter and increase in viscosity during storage. Furthermore, when the cosmetic containing the composition of the present invention is applied to the hair, it can give a desirable moist feeling and softness.

As the component (C), gluconic acid or gluconolactone may be blended alone, or gluconic acid and gluconolactone may be blended together. However, gluconic acid is a hydrolyzate of gluconolactone, and gluconic acid and gluconolactone are in equilibrium in the presence of water. Therefore, even when gluconic acid or gluconolactone is compounded alone, a composition containing both gluconic acid and gluconolactone may be obtained.

The mass ratio (C)/(B) of component (C) gluconic acid and/or gluconolactone to component (B) fatty acid amidoamine is within the range of 0.2 to 2.8 (0.2 or more and 2.8 or less). When gluconic acid and/or gluconolactone are not compounded, or when the mass ratio (C)/(B) is less than 0.2, there is a risk that component (A), component (B), or ion complexes thereof cannot be completely dissolved, and disperses or precipitates as an insoluble matter; and the insoluble matter tends to precipitate during storage of the composition, and the storage stability aimed at by the invention cannot be obtained.

On the other hand, when the mass ratio (C)/(B) is greater than 2.8, there is a risk of impairing the feeling of use, such as stickiness when the cosmetic composition containing the transparent liquid composition of the present invention is applied to the hair. Also, storage stability tends to decrease.

The mass ratio (C)/(B) is preferably in the range of 0.5 to 2.0. Within this range, precipitation of insoluble matter during storage of the composition can be more reliably suppressed, and it is possible to more reliably prevent the occurrence of stickiness.

The preferable range of the content of component (C) gluconic acid and/or gluconolactone in the transparent liquid composition of the present invention is not particularly limited as long as the above composition ratio is satisfied, but the content is preferably 5 to 25% by mass and more preferably 10 to 20% by mass.

Any commercially available gluconic acid can be used for producing the transparent liquid composition of the present invention. For example, one commercially available as a 50% aqueous solution can be used. Any commercially available gluconolactone can also be used.

[About Component (D) (Polyhydric Alcohol)]

The polyhydric alcohol used as component (D) is not particularly limited as long as it is an alcohol having two or more hydroxyl groups in the molecule and is conventionally used in cosmetics. For example, glycerols such as glycerin, diglycerin, and polyglycerin, propylene glycol (1,2-propanediol), 1,3-butylene glycol (1,3-butanediol), pentylene glycol (1,2-pentanediol), hexylene glycol (2-methyl-2,4-pentanediol), 1,2-hexanediol, 1,6-hexanediol, neopentyl glycol, isoprene glycol, ethylene glycol, glycols such as low polymer polyethylene glycol and sugar alcohols such as maltitol, erythritol, mannitol, xylitol and sorbitol.

Among the polyhydric alcohols exemplified above, glycerols or glycols are preferably used because they are in the effect of maintaining the transparent liquid composition of the present invention in a uniform liquid state, and among them, glycerin, 1,3-butylene glycol, pentylene glycol and hexylene glycol are particularly preferred. These polyhydric alcohols can be used singly or in combination of two or more.

The preferable range of the content of the component (D) polyhydric alcohol in the transparent liquid composition of the present invention is not particularly limited, but the content is preferably 5 to 35% by mass, more preferably 7 to 25% by mass, based on the total amount of the transparent liquid composition, from the viewpoint of more reliably suppressing precipitation of insoluble matter during storage, which is the object of the present invention.

[Other Components in the Transparent Liquid Composition]

The transparent liquid composition of the present invention contains a solvent such as water in addition to the above components (A), (B), (C) and (D), and can further contain other components as necessary. As the solvent, in addition to water, alcohols other than (D) polyhydric alcohols, such as lower alcohols such as ethanol, can be used.

Examples of other components that can be contained as necessary include anionic surfactants, nonionic surfactants, amphoteric surfactants, cationic surfactants other than component (B), synthetic polymers such as cationic polymers, amphoteric polymers, and anionic polymers, semi-synthetic polymers, polysaccharides and their derivatives, animal and plant oils, hydrocarbons, ester oils, higher alcohols, thickeners, animal and plant extracts, silicones, preservatives, fragrances, ultraviolet rays protective agents, and moisturizing agents. In addition to these, other ingredients can be added as appropriate within the range that does not impair the characteristics when the transparent liquid composition of the present invention is compounded in the cosmetic.

[Method for Producing a Transparent Liquid Composition]

The transparent liquid composition of the present invention is manufactured by mixing and dissolving the above components (A), (B), (C), (D), a solvent such as water, and other components added as necessary by a conventional method.

[Cosmetics Containing the Transparent Liquid Composition of the Present Invention]

The transparent liquid composition of the present invention is excellent in the effect of imparting favorable feeling such as softness and moist feeling in addition to smoothness and luster to hair that has lost its hydrophobicity due to damage and has decreased smoothness and luster. Therefore, it is suitable for use in hair cosmetics that improve the condition of hair.

Examples of hair cosmetics that improve the condition of hair by compounding the transparent liquid composition of the present invention include hair treatments, hair conditioners, system treatments, shampoos, hair mists, split ends coats, hair creams, first and second agents for permanent wave, hair straighteners, set lotions, hair waxes, styling agents, hair dyes, liquid hair styling agents, hair tonics and hair growth agents.

Furthermore, the transparent liquid composition of the present invention may be compounded in skin cosmetics. Examples of the skin cosmetics includes cleansing creams, emollient creams, hand creams, aftershave lotions, shaving foams, facial cleansing creams, facial cleansers, body shampoos, various soaps, hair removers, face packs, milky lotions, lotions, make-up products, and sunscreen products. In that case, the effect of imparting softness, moisturizing properties, and adaptability to the skin can be expected.

The transparent liquid composition of the present invention is easy to maintain a uniform solution state without precipitation of insoluble matter or increase in viscosity even during storage, and it exhibits excellent handling properties in the production of cosmetics that incorporate it. The preparation can be carried out without a step of heating, although it is preferable to heat the mixture during mixing in order to obtain a uniform solution.

The preferred range of the amount of the transparent liquid composition of the present invention to be compounded into the cosmetic (content in the cosmetic) varies depending on the type of cosmetic, and is not particularly limited, but 0.5 to 15% by mass is preferred in many cases, and particularly 1.0 to 10% by mass is more preferred in many cases. When the amount of the composition in the cosmetic is small, there is a risk that the effect of imparting smoothness, luster, softness and moistness to damaged hair may not be sufficiently exhibited in hair cosmetics. Further, even when the compounding amount of the transparent liquid composition of the present invention is increased beyond a certain amount, the corresponding improvement in effect is not observed.

Cosmetics compounded with the transparent liquid composition of the present invention may appropriately contain other components commonly used in cosmetics, such as oils, surfactants, polymer compounds such as thickeners, moisturizing agents, whitening agents, texture improvers, chemicals, UV absorbers, antioxidants, sequestering agents, pH adjusters, preservatives, pigments, coloring agents, fragrances, etc, other than components (A) to (D) and water.

The oils are not particularly limited as long as they are oil agents that are commonly used in cosmetics, and any oil agents can be used, regardless of the origin of volatile or non-volatile and animal oil, vegetable oil or synthetic oil, etc. Examples thereof include hydrocarbon oil, fat, ester oil, fatty acid, triacylglycerol, higher alcohol, silicone oil, fluorine oil, lanolin derivative and oil such as wax. Specific examples include hydrocarbon oils such as (C13-15)alkane, (C15-19)alkane, (C18-21)alkane, (C21-28)alkane, (C10, 11)isoparaffin, (C10-13)isoparaffin, (C13, 14)isoparaffin, (C13-16)isoparaffin, isododecane, isohexadecane, liquid paraffin, heavy liquid isoparaffin, α-olefin oligomer, squalane, polyisobutene, and polybutene; oils such as *Theobroma grandiflorum* seed fat, mango seed fat, cocoa butter, palm oil, palm kernel oil, coconut oil, shea butter, shoreastenoptera butter, african mango tree kernel fat, avocado butter, sarasoju seed fat, astropotassium murumuru fat, astropotassium murumuru seed fat, astropotassium tsukuma seed oil, garcinia indica seed oil, tricilia emetica seed oil, basiaratifolia seed oil, garcinia indica seed oil, hydrogenated cacao butter, (macadamia seed oil/hydrogenated macadamia seed oil)esters, and milk fat;

ester oils such as jojoba oil, diisobutyl adipate, 2-hexyldecyl adipate, di-2-heptylundecyl adipate, alkylglycol monoisostearate, isocetyl isostearate, trimethylolpropane triisostearate, ethyleneglycol di-2-ethylhexanoate, cetyl 2-ethylhexanoate, neopentyl glycol di-2-ethylhexanoate, trimethylolpropane tri-2-ethylhexanoate, pentaerythritol tetra-2-ethylhexanoate, cetyl 2-ethylhexanoate, oleic acid oleyl, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, dipentaerythritol fatty acid ester, isononyl isononanoate, isotridecyl isononanoate, isopropyl myristate, isopropyl palmitate, 2-octyldodecyl myristate, 2-hexyldecyl myristate, myristyl myristate, hexyldecyl dimethyloctanoate, ethyl laurate, hexyl laurate, 2-ethylhexyl methoxycinnamate, and diisostearyl malate; trifatty acid glyceryl such as glyceryl triisooctanoate, glyceryl triisostearate, diglyceryl diisostearate, diglyceryl triisostearate, diglyceryl tetraisostearate, decaglyceryl decaisostearate, glyceryl triisopalmitate, glyceryl trimyristate, isostearic/myristic diglycerides, tridecyl trimellitate, and tri(caprylic/capric) glyceryl;

amino acid oils such as N-lauroyl-L-glutamic acid-2-octyldodecyl ester, and N-lauroyl-L-glutamic acid di(phytostearyl/2-octyldodecyl);

fatty acids such as isostearic acid and oleic acid;

higher alcohols such as oleyl alcohol, and isostearyl alcohol;

cyclic silicone oils such as cyclotetrasiloxane, cyclopentasiloxane, and cyclohexasiloxane;

chain silicone oils such as dimethylpolysiloxane, methylphenylpolysiloxane, alkoxy-modified organopolysiloxane, and fluorine-modified silicone;

fluorinated oils such as perfluoro polyethers;

lanolin derivatives such as lanolin, lanolin acetate, lanolin fatty acid isopropyl and lanolin alcohol; and waxes such as carnauba wax, candelilla wax, beeswax, rice bran wax, shellac wax, whale wax and sunflower seed wax.

Examples of Surfactants Include nonionic surfactants, which include polyglyceryl fatty acid esters such as polyglyceryl-2 dipolyhydroxystearate, PEG-30 dipolyhydroxystearate, polyglyceryl-6 polyricinoleate, polyglyceryl-6 laurate, and polyglyceryl-2 isostearate;

alkyl glucosides such as decylglucoside, (caprylyl/capryl) glucoside, cetearyl glucoside, arachyl glucoside, (C12-20)alkyl glucoside, coconut oil alkyl glucoside, myristyl glucoside, heptyl glucoside, and lauryl glucoside, sorbitan fatty acid esters such as sorbitan monolaurate, and sorbitan monopalmitate, glycerin fatty acid esters and alkylene oxide adducts thereof, polyoxyalkylene alkyl ethers, polyoxyalkylene fatty acid esters, polyoxyalkylene alkylphenols, polyoxyethylene sorbitol fatty acid esters, polyoxyethylene alkylphenyl formaldehyde condensation, polyoxyethylene sterols and derivatives thereof, polyoxyethylene lanolin and derivatives thereof, polyoxyethylene beeswax derivatives, sucrose fatty acid esters, polyoxyethylene hydrogenated castor oil, polyoxyethylene castor oil, and the like;

anionic surfactants which include higher fatty acid soap, alkyl sulfate, alkyl phosphate, polyoxyethylene alkyl ether sulfate, polyoxyethylene alkylphenyl ether sulfate, alkyl ether phosphate, alkyl ether carboxylate, acylmethyl taurine, N-acyl-N-methyl-β-alanine salts, N-acylglycinates, N-acylglutamates, polyoxyethylene alkylcarboxylates, alkylphenyl ether sulfonates, alkylsulfosuccinic acid and its salts, N-acylsarcosine and its salts, polyoxyethylene coconut oil fatty acid monoethanolamide sulfate, lauroyl oat amino acid and its salts, cocoyl malic amino acid and its salts, and the like;

cationic surfactants which include alkylamine salts such as monoalkylamine salts, dialkylamine salts and trialkylamine salts, fatty acid amide alkylamines such as stearamidoethyldiethylamine and stearamidopropyldimethylamine, alkyl quaternary ammonium salts such as monoalkyl type quaternary ammonium salts, dialkyl type quaternary ammonium salts, trialkyl type quaternary ammonium salts, and benzalkonium type quaternary ammonium salts, cyclic quaternary ammonium salts such as alkylpyridinium salts, benzethonium chloride, and the like;

silicone surfactants which include

PEG-11 methylether dimethicone, PEG/PPG-20/22 butylether dimethicone, PEG-9 dimethicone, PEG-3 dimethicone, PEG-9 methylether dimethicone, PEG-10 dimethicone, PEG-32 methylether dimethicone, cetyl PEG/PPG-10/1 dimethicone, PEG-9 polydimethylsiloxyethyl dimethicone, lauryl PEG-9 polydimethylsiloxyethyl dimethicone, polyether-modified silicone such as methylpolysiloxane/cetylmethylpolysiloxane/poly(oxyethylene/oxypropylene) methylpolysiloxane copolymer, poly(oxyethylene/oxypropylene) methylpolysiloxane copolymer, and (dimethicone/(PEG-10/15)) crosspolymer, polyglycerin-modified silicones such as polyglyceryl-3 polydimethyl siloxyethyl dimethicone, and lauryl polyglyceryl-3 polydimethylsiloxyethyl dimethicone, dimethylsiloxane/methylcetylsiloxane copolymer, and the like; and amphoteric surfactants which include alkyldimethylamino acetic acid betaine, alkylamidoamino acetic acid betaine, fatty acid amidopropyldimethylamino acetic acid betaine, 2-alkyl-N-carboxy-N-hydroxyimidazolinium betaine, alkylglycinate, carboxymethylglycinate, N-acylaminoethyl-N-2-hydroxyethylglycinate, alkylaminopropionate, alkyliminodipropionate, alkylhydroxysulfobetaine, and the like.

Polymer compounds such as thickeners are not particularly limited as long as they are commonly used in cosmetics, and examples thereof include acrylic thickeners; cellulosic thickeners such as methylcellulose, ethylcellulose, hydroxyethyl cellulose, hydroxymethyl cellulose, hydroxypropyl cellulose, hydroxypropyl methylcellulose, carboxymethylcellulose, carboxyethylcellulose, stearoxyhydroxypropyl methylcellulose, nitrocellulose, and sodium cellulose sulfate; microbial thickeners such as xanthan gum, hydroxypropylxanthan gum, gum arabic, tragacanth gum, cabrogum, guar gum, and dextran;

thickeners including polyvinyl alcohol, high molecular weight dimethylpolysiloxane, pectin, agar, quince seed, starch, algecolloid, succinoglucan, collagen, gelatin, casein, albumin, carboxymethyl starch, sodium alginate, polyvinyl methylether, sodium polyacrylate, polyethylene acrylate, cationic polymers; and other polymer compounds.

Examples of the acrylic acid thickener include polyacrylamide, (hydroxyethyl acrylate/Na acryloyldimethyltaurate) copolymer, (Na acrylate/Na acryloyldimethyltaurate) copolymer, (acrylamide/ammonium acrylate) copolymer, (Na acrylate/acryloyldimethyltaurine/dimethylacrylamide) crosspolymer, polyacrylate-13, polyacrylate crosspolymer-6, (acrylamidopropyltrimonium chloride/acrylates) copolymer, (acryloyldimethyltaurate ammonium/vinylpyrrolidone) copolymer, (acryloyl ammonium dimethyl taurate/beheneth-25 methacrylate) crosspolymer, (acryloyl dimethyl taurate ammonium/steareth-25 methacrylate) crosspolymer, (acrylates/alkyl acrylate (C10-30)) crosspolymer, (acrylates/steareth-20 methacrylate)copolymer, (acrylates/beheneth-25 methacrylate) copolymer, (acrylates/steareth-20 itaconate) copolymer, steareth-10 allyl ether/acrylates copolymer, and carboxyvinyl polymer.

Examples of the moisturizers include glycerin, ethoxydiglycol, propylene glycol, maltitol, sorbitol, 1,3-butylene glycol, sodium lactate, polyethylene glycol, sodium pyrrolidonecarboxylate, and sodium hyaluronate. Examples of the whitening agents include ascorbic acid derivatives such as ellagic acid, chamomile extract, licorice extract, lucinol, rosemary extract, arhutin, tranexamic acid, 4-methoxysalicylic acid potassium salt, ascorbic acid, ascorbic acid glucoside, glyceryl ascorbic acid, and magnesium ascorbyl phosphate.

Examples of the texture modifiers include amylopectin (amylose), acylated amino acids, polymethyl methacrylate, boron nitride, silica, alumina, aluminum hydroxide, metal soap, silicone powder, and dimethyl silylated silica.

Agents may include anti-roughness agents or anti-inflammatory agents. Examples of the anti-roughness agents and anti-inflammatory agents include dipotassium glycyrrhizinate, stearyl glycyrrhetinate, methyl salicylate, pyridoxine hydrochloride, allantoin, sea salt, sorghum extract, aloe extract, gardenia extract, chamomile extract, licorice extract, sapindactyl extract, and chinese ginseng extract, scutellaria root extract, tencha extract, loquat extract, *Ginkgo biloba* extract, hypericum extract, yarrow extract, safflower extract, spruce extract, salvia extract, white birch extract, chimp extract, tonin extract, neil extract, althea extract, arnica extract, carrot extract, peony extract, cnidium extract, gentian extract, cordyceps extract, phellodendron extract, inchinko extract, gennoshoko extract, peach leaf extract, kumazasa extract, coix extract, horse chestnut extract, hawthorn extract, coptis extract, ganoderma extract, calendula extract, peppermint extract, comfrey extracts, butcher bloom extracts, malva extracts, cornflower extracts, and prickly pear extracts. Other than the above, hair growth agents, acne agents, dandruff/itch agents, armpit odor prevention agents, and the like can be mentioned as the agents.

Examples of the UV absorbers include benzophenone derivatives such as 2-hydroxy-4-methoxybenzophenone, sodium 2-hydroxy-4-methoxybenzophenone-5-sulfonate, sodium dihydroxydimethoxy benzophenone-sulfonate, 2,4-dihydroxybenzophenone, and tetrahydroxybenzophenone;

para-aminobenzoic acid derivatives such as para-aminobenzoic acid, ethyl para-aminobenzoate, glyceryl para-aminobenzoate, amyl para-dimethylaminobenzoate, and octyl para-dimethylaminobenzoate;

methoxycinnainic acid derivatives such as ethyl para-methoxycinnamate, isopropyl para-methoxycinnamate, 2-ethylhexyl para-methoxycinnamate (ethylhexyl methoxycinnamate), sodium para-methoxycinnamate, potassium para-methoxycinnamate, and glyceryl mono-2-ethylhexanoate di-para-methoxycinnamate;

salicylic acid derivatives such as octyl salicylate, phenyl salicylate, homomenthyl salicylate, dipropylene glycol salicylate, ethylene glycol salicylate, myristyl salicylate, and methyl salicylate;

urocanic acid, ethyl urocanate, 4-tert-butyl-4'-methoxydibenzoylmethane (t-butylmethoxydibenzoylmethane), 2-(2'-hydroxy-5'-methylphenyl) benzotriazole, methyl anthranilate, octocrylene (2-cyano-3,3-diphenylprop-2-enoate-2-ethylhexyl), 2-(4-diethylamino-2-hydroxybenzoyl)hexylbenzoate (diethylaminohydroxybenzoylhexylbenzoate), ethylhexyltriazone, and bisethylhexyloxyphenol methoxyphenyltriazine.

Examples of the antioxidants include sodium pyrosulfite, vitamin E and derivatives thereof, tannin, and BHT (butylhydroxytoluene).

Examples of the sequestering agents include edetate sodium salt, phosphoric acid, citric acid, phytic acid, etidronic acid, and glutamic acid diacetic acid sodium salt.

Examples of the pH adjusters include lactic acid, citric acid, glycolic acid, succinic acid, tartaric acid, malic acid, potassium carbonate, sodium hydrogencarbonate and ammonium hydrogencarbonate.

Examples of the antiseptics include 1,2-alkanediols such as 1,2-pentanediol and 1,2-hexanediol, paraoxybenzoic acid alkyl esters such as methylparaben and propylparaben, benzoic acid, sodium benzoate, sorbic acid, sodium sorbate, phenoxyethanol, and glyceryl monoalkyl ethers such as ethylhexylglycerin.

The above components that are commonly used in cosmetics can be used singly or in combination of two or more.

EXAMPLE

Next, the present invention will be described in detail with reference to examples, but the scope of the present invention is not limited only to the examples, and various modifications can be made within the same or equivalent range as the scope of the claims. In addition, unless otherwise specified, all percentages written in Examples and the like are percentages by mass.

Example 1: Preparation of a Composition (Clear Liquid Composition) Containing Hydrolyzed Soy Protein, Stearamidopropyldimethylamine, Gluconic Acid and Pentylene Glycol In a beaker, 40 g of 25% aqueous solution of hydrolyzed soy protein (number average molecular weight: 700), 12 g of stearamidopropyl dimethylamine, 28 g of 50% gluconic acid aqueous solution, 15 g of pentylene glycol and 5 g of water were mixed, and, then, dissolved by heating and stirring at 40-60° C., followed by cooling to room temperature, to obtain 100 g of composition titled above.

Example 2: Preparation of a Composition Containing Hydrolyzed Pea Protein, Stearamidopropyldimethylamine, Gluconic Acid and 1,3-Butylene Glycol Except for using a 25% aqueous solution of hydrolyzed pea protein (number average molecular weight: 500) instead of a 25% aqueous solution of hydrolyzed soy protein, and using 1,3-butylene glycol instead of pentylene glycol, 100 g of the composition titled above was obtained according to the same manner as in Example 1.

Example 3: Preparation of a Composition Containing Hydrolyzed Rice Protein, Stearamidoethyldiethylamine, Gluconic Acid and Glycerin By mixing 40 g of a 25% aqueous solution of hydrolyzed rice protein (number average molecular weight: 400), 7 g of stearamidoethyldiethylamine, 10 g of a 50% gluconic acid aqueous solution, 25 g of glycerin, and 18 g of water, and dissolving them by heating and stirring, followed by cooling to room temperature, 100 g of the composition titled above was obtained.

Example 4: Preparation of a Composition Containing Hydrolyzed Keratin, Stearamidoethyldiethylamine, Gluconic Acid and Hexylene Glycol By mixing 15 g of powder of hydrolyzed keratin (number average molecular weight: 1000), 12 g of stearamidoethyldiethylamine, 40 g of 50% gluconic acid aqueous solution, 20 g of hexylene glycol, and 13 g of water, and dissolving them by heating and stirring, followed by cooling to room temperature, 100 g of the composition titled above was obtained.

Example 5: Preparation of a Composition Containing Hydrolyzed Soy Protein, Stearamidopropyldimethylamine, Gluconic Acid and Hexylene Glycol By mixing 20 g of a 25% aqueous solution of hydrolyzed soy protein (number average molecular weight: 700), 7 g of stearamidopropyl dimethylamine, 14 g of 50% gluconic acid aqueous solution, 7.5 g of hexylene glycol, and 51.5 g of water, and dissolving them by heating and stirring, followed by cooling to room temperature, 100 g of the composition titled above was obtained.

Example 6: Preparation of a Composition Containing Alanine, Stearamido Propyldimethylamine, Gluconic Acid and Pentylene Glycol By mixing 10 g of alanine powder, 12 g of stearamidopropyl dimethylamine, 28 g of 50% gluconic acid aqueous solution, 15 g of pentylene glycol and 35 g of water, and dissolving them by heating and stirring, followed by cooling to room temperature, 100 g of the composition titled above was obtained.

Example 7: Preparation of a Composition Containing Proline, Stearamido Propyldimethylamine, Gluconic Acid and Pentylene Glycol According to the same manner as in Example 6, except that 10 g of proline powder was used instead of 10 g of alanine powder, 100 g of the composition titled above was obtained.

Comparative Example 1: Preparation of a Composition Containing Hydrolyzed Soy Protein, Stearamidopropyldimethylamine and Pentylene Glycol By mixing 40 g of a 25% aqueous solution of hydrolyzed soy protein (number average molecular weight: 700), 12 g of stearamidopropyl dimethylamine, 15 g of pentylene glycol, and 33 g of water, and dissolving them by heating and stirring at 40 to 60° C., followed by cooling to room temperature, 100 g of the composition titled above was obtained.

Comparative Example 2: Preparation of Composition Containing Hydrolyzed Rice Protein and Stearamidopropyldimethylamine By mixing 25 g of hydrolyzed rice protein powder (number average molecular weight: 400), 21 g of stearamidopropyldimethylamine, and 54 g of water, and dissolving them by heating and stirring, followed by cooling to room temperature, 100 g of the composition titled above was obtained.

Comparative Example 3: Preparation of a Composition Containing Hydrolyzed Rice Protein, Stearamidoethyldiethylamine and Glycerin By mixing 10 g of hydrolyzed rice protein powder (number average molecular weight: 400), 7 g of stearamidoethyldiethylamine, 25 g of glycerin, and 58 g of water, and dissolving them by heating and stirring, followed by cooling to room temperature, 100 g of the composition titled above was obtained.

Comparative Example 4: Preparation of Composition Containing Hydrolyzed Rice Protein, Stearamidoethyldiethylamine, Gluconic Acid and Glycerin (1)

By mixing 10 g of hydrolyzed rice protein powder (number average molecular weight: 400), 7 g of stearamidoethyldiethylamine, 2 g of 50% gluconic acid aqueous solution, 25 g of glycerin, and 56 g of water, and dissolving them by heating and stirring, followed by cooling to room temperature, 100 g of the composition titled above was obtained.

Comparative Example 5: Preparation of Composition Containing Hydrolyzed Rice Protein, Stearamidoethyldiethylamine, Gluconic Acid and Glycerin (2)

By mixing 10 g of hydrolyzed rice protein powder (number average molecular weight: 400), 7 g of stearamidoethyldiethylamine, 40 g of 50% gluconic acid aqueous solution, 25 g of glycerin, and 18 g of water, and dissolving them by heating and stirring, followed by cooling to room temperature, 100 g of the composition titled above was obtained.

Comparative Example 6: Preparation of a Composition Containing Alanine, Stearamidopropyldimethylamine and Pentylene Glycol By mixing 10 g of alanine powder, 12 g of stearamidopropyl dimethylamine, 15 g of pentylene glycol, and 63 g of water, and dissolving them by heating and stirring, followed by cooling to room temperature, 100 g of the composition titled above was obtained.

Comparative Example 7: Preparation of a Composition Containing Proline, Stearamidopropyldimethylamine and Pentylene Glycol According to the same manner as in Comparative Example 6 except that 10 g of proline powder was used instead of 10 g of alanine powder, 100 g of the composition titled above was obtained.

[Evaluation of Solubility]

Appearances of the compositions (stored in glass bottles) prepared in Examples 1 to 7 and Comparative Examples 1 to 7 were visually observed and evaluated according to the following criteria. The results are shown in Table 1. The numerical values in Table 1 represent the mass ratio of the compounding component.

○: A transparent and uniform liquid was observed.

Δ: A turbid liquid in which insoluble matter was precipitated and dispersed was observed.

x: Insoluble matter deposits and precipitates.

[Evaluation of Storage Stability]

The compositions prepared in Examples 1 to 7 and Comparative Examples 1 to 7 (stored in glass bottles) were stored at 5° C. for 1 month and then returned to room temperature. The appearances of them were visually confirmed and evaluated according to the following criteria.

○: A transparent, uniform liquid or a fluid liquid in which a small amount of insoluble matter is dispersed.

Δ: Fluid liquid with insoluble matter precipitated and deposited.

x: Losing fluidity and semi-solid.

TABLE 1

| | | Example | | | | | | | Comparative example | | | | | | |
|---|---|---|---|---|---|---|---|---|---|---|---|---|---|---|---|
| | Ingredients | 1 | 2 | 3 | 4 | 5 | 6 | 7 | 1 | 2 | 3 | 4 | 5 | 6 | 7 |
| (A) | hydrolyzed soy protein | 10 | — | — | — | 5 | — | — | 10 | — | — | — | — | — | — |
| | hydrolyzed pea protein | — | 10 | — | — | — | — | — | — | — | — | — | — | — | — |
| | hydrolyzed rice protein | — | — | 10 | — | — | — | — | — | 25 | 10 | 10 | 10 | — | — |
| | hydrolyzed keratin | — | — | — | 15 | — | — | — | — | — | — | — | — | — | — |
| | alanine | — | — | — | — | — | 10 | — | — | — | — | — | — | 10 | — |
| | proline | — | — | — | — | — | — | 10 | — | — | — | — | — | — | 10 |
| (B) | stearamidopropyl dimethylamine | 12 | 12 | — | — | 7 | 12 | 12 | 12 | 21 | — | — | — | 12 | 12 |
| | stearamidoethyl diethylamine | — | — | 7 | 12 | — | — | — | — | — | 7 | 7 | 7 | — | — |
| (C) | gluconic acid | 14 | 14 | 5 | 20 | 7 | 14 | 14 | — | — | — | 1 | 20 | — | — |
| (D) | 1,3-butylene glycol | — | 15 | — | — | — | — | — | — | — | — | — | — | — | — |
| | pentylene glycol | 15 | — | — | — | — | 15 | 15 | 15 | — | — | — | — | 15 | 15 |
| | hexylene glycol | — | — | — | 20 | 7.5 | — | — | — | — | — | — | — | — | — |
| | glycerin | — | — | 25 | — | — | — | — | — | — | 25 | 25 | 25 | — | — |
| Water | | Amount that makes a total of 100 | | | | | | | | | | | | | |
| Solubility | | ○ | ○ | ○ | ○ | ○ | ○ | ○ | Δ | ○ | Δ | Δ | ○ | Δ | Δ |
| Storage stability | | ○ | ○ | ○ | ○ | ○ | ○ | ○ | × | × | × | × | Δ | × | × |

As shown in Table 1, the compositions of Examples 1 to 7, which were prepared with peptides (protein hydrolysates) or amino acids, fatty acid amidoamines, gluconic acid and polyhydric alcohols within specific mass % and mass ratio ranges, were in a uniform solution state, and were stable without precipitation of insoluble matter even after storage for one month. On the other hand, the compositions of Comparative Examples 1, 2, 3, 6 and 7, not containing gluconic acid (and gluconolactone), did not become homogeneous after preparation, and precipitates were observed after storage. Similarly, in Comparative Example 4 in which the mass ratio is less than 0.2 (1/7), the composition, though containing gluconic acid, did not become homogeneous after preparation, and precipitates was observed after storage. In Comparative Example 5, in which the mass ratio exceeds 2.8 (20/7), the composition became uniform after preparation, but a slight amount of precipitation was confirmed after storage.

In addition, when the compositions of Example 1 and Comparative Example 1 were stored at 5° C. for 1 month, the composition of Example 1 maintained a fluid, low-viscosity and transparent solution state, and it is clear that the handleability is excellent. On the other hand, in the composition of Comparative Example 1, insoluble matter precipitated after storage, the viscosity of the composition increased and the fluidity decreased, which clearly poses a problem of handling.

Examples 8-14, Comparative Examples 8-11 and Control Example 1

Hair Treatment

Hair treatments having the compositions shown in Table 2, which contain the compositions of Examples 1 to 7 and the compositions of Comparative Examples 3 and 5 to 7, were prepared as Examples 8 to 14 and Comparative Examples 8 to 11, respectively. Furthermore, a hair treatment containing no composition was prepared as Control Example 1. Table 2 shows the compounding ratio (mass ratio) of the compounding components of each hair treatment.

TABLE 2

| | Example | | | | | | | Comparative example | | | | Control |
|---|---|---|---|---|---|---|---|---|---|---|---|---|
| | 8 | 9 | 10 | 11 | 12 | 13 | 14 | 8 | 9 | 10 | 11 | 1 |
| Composition of Example 1 | 2.0 | — | — | — | — | — | — | — | — | — | — | — |
| Composition of Example 2 | — | 2.0 | — | — | — | — | — | — | — | — | — | — |
| Composition of Example 3 | — | — | 2.0 | — | — | — | — | — | — | — | — | — |
| Composition of Example 4 | — | — | — | 2.0 | — | — | — | — | — | — | — | — |
| Composition of Example 5 | — | — | — | — | 2.0 | — | — | — | — | — | — | — |
| Composition of Example 6 | — | — | — | — | — | 2.0 | — | — | — | — | — | — |
| Composition of Example 7 | — | — | — | — | — | — | 2.0 | — | — | — | — | — |
| Composition of Comparative Example 3 | — | — | — | — | — | — | — | 2.0 | — | — | — | — |
| Composition of Comparative Example 5 | — | — | — | — | — | — | — | — | 2.0 | — | — | — |
| Composition of Comparative Example 6 | — | — | — | — | — | — | — | — | — | 2.0 | — | — |
| Composition of Comparative Example 7 | — | — | — | — | — | — | — | — | — | — | 2.0 | — |
| Liquid paraffin#70S | 1.0 | 1.0 | 1.0 | 1.0 | 1.0 | 1.0 | 1.0 | 1.0 | 1.0 | 1.0 | 1.0 | 1.0 |
| Cetyl alcohol | 1.5 | 1.5 | 1.5 | 1.5 | 1.5 | 1.5 | 1.5 | 1.5 | 1.5 | 1.5 | 1.5 | 1.5 |
| Stearyl alcohol | 1.0 | 1.0 | 1.0 | 1.0 | 1.0 | 1.0 | 1.0 | 1.0 | 1.0 | 1.0 | 1.0 | 1.0 |
| Stearyltriethylammonium chloride (25%) | 2.8 | 2.8 | 2.8 | 2.8 | 2.8 | 2.8 | 2.8 | 2.8 | 2.8 | 2.8 | 2.8 | 2.8 |
| Methylpolysiloxane 100 cc | 2.0 | 2.0 | 2.0 | 2.0 | 2.0 | 2.0 | 2.0 | 2.0 | 2.0 | 2.0 | 2.0 | 2.0 |
| Phenoxyethanol | 0.5 | 0.5 | 0.5 | 0.5 | 0.5 | 0.5 | 0.5 | 0.5 | 0.5 | 0.5 | 0.5 | 0.5 |
| Purified water | Amount that makes a total of 100 | | | | | | | | | | | |

The hair bundles damaged by the [Bleaching treatment] shown below were treated with the hair treatments of Examples 8 to 14, Comparative Examples 8 to 11 and Control Example 1 prepared as described above, according to [Hair treatment] shown below, and subjected to the [Sensory test] shown below.

[Bleaching Treatment]

A hair bundle having a length of 15 cm and a weight of 1.5 g was immersed in an aqueous solution containing 3% hydrogen peroxide and 1% ammonia at 30° C. for 30 minutes, and then washed with tap water. By repeating this treatment five times, the bleaching treatment was performed.

[Hair Treatment]

The bleached hair bundles were washed with a 2% polyoxyethylene (3) sodium lauryl ether sulfate aqueous solution. Each of these hair bundles was treated with 2 g of each of the hair treatments of Examples 8 to 14, Comparative Examples 8 to 11 and Control Example 1, rinsed with running water, and dried with a hair dryer. This washing with the polyoxyethylene (3) sodium lauryl ether sulfate aqueous solution, treatment with hair treatment, rinsing with running water, and drying with a dryer were each repeated five times.

[Sensory Test]

The hair bundles treated with the hair treatments of Examples 8 to 14 and Comparative Examples 8 to 11 were subjected to blind evaluation (blind test) by 10 panelists for the three items of smoothness, moist feeling, and softness. Evaluation is based on Control Example 1, <2 points> if very good, <1 point> if good, <−1 point> if bad, and <−2> if very bad, compared to Control Example 1. If it is the same as Control Example 1, it is scored as <0 point>, and the total score for each evaluation item is used for evaluation. The results are shown in Table 3 below.

TABLE 3

| | Example | | | | | | | Comparative example | | | |
|---|---|---|---|---|---|---|---|---|---|---|---|
| | 8 | 9 | 10 | 11 | 12 | 13 | 14 | 8 | 9 | 10 | 11 |
| Smoothness | 12 | 10 | 11 | 10 | 11 | 10 | 10 | 9 | 8 | 9 | 9 |
| Moist feeling | 12 | 11 | 10 | 9 | 12 | 14 | 10 | 9 | 7 | 9 | 9 |
| Softness | 12 | 11 | 9 | 8 | 11 | 10 | 14 | 8 | 7 | 8 | 9 |

As shown in Table 3, the hair treatments of Examples 8 to 14 gave the same or better feeling in use in terms of smoothness, moistness and softness than the hair treatments of Comparative Examples 8 to 11. In addition, in Comparative Example 9, where the hair treatment using Comparative Example 5 in which the mass ratio (C)/(B) of (C) to component (B) exceeded 2.0 is used, the result was that the feeling of use was inferior compared to any examples.

What is claimed is:

1. A transparent liquid composition which contains (A) one or more compounds selected from the group consisting of peptides and amino acids, (B) a fatty acid amidoamine represented by formula (I) below, (C) gluconic acid and/or gluconolactone, and (D) a polyhydric alcohol, wherein the contents of (A), (B), (C) and (D) are 3 to 15% by mass, 5 to 15% by mass, 5 to 25% by mass, and 5 to 35% by mass respectively, based on the total mass of the composition, and (C)/(B), the mass ratio of (C) gluconic acid and/or gluconolactone to (B) fatty acid amidoamine, is 0.5 to 2.0:

(I)

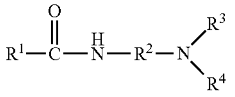

wherein $R^1$ represents a saturated or unsaturated chain hydrocarbon having 11 to 25 carbon atoms or a saturated or unsaturated cyclic hydrocarbon having 11 to 25 carbon atoms, $R^2$ represents an alkylene group having 1 to 3 carbon atoms, and $R^3$ and $R^4$ each represent an alkyl group having 1 to 3 carbon atoms.

2. The transparent liquid composition according to claim 1, wherein the (A) one or more compounds selected from the group consisting of peptides and amino acids is a compound selected from the group consisting of vegetable protein hydrolysates and keratin hydrolysates.

3. The transparent liquid composition according to claim 1, wherein the (D) polyhydric alcohol is one or more selected from the group consisting of 1,3-butylene glycol, pentylene glycol, hexylene glycol and glycerin.

4. A cosmetic containing the transparent liquid composition according to claim 1.

5. The cosmetic according to claim 4 which is a hair cosmetic that improves the condition of hair.

6. The transparent liquid composition according to claim 2, wherein the (D) polyhydric alcohol is one or more selected from the group consisting of 1,3-butylene glycol, pentylene glycol, hexylene glycol and glycerin.

7. The transparent liquid composition according to claim 1, wherein (C)/(B), the mass ratio of (C) gluconic acid and/or gluconolactone to (B) fatty acid amidoamine, is 0.7 to 2.0.

8. The transparent liquid composition according to claim 2, wherein (C)/(B), the mass ratio of (C) gluconic acid and/or gluconolactone to (B) fatty acid amidoamine, is 0.7 to 2.0.

* * * * *